(12) United States Patent
Patel

(10) Patent No.: US 7,662,360 B2
(45) Date of Patent: Feb. 16, 2010

(54) CONJUGATES OF N-HYDROXYPROPYMETHACRYLAMIDE-METHACRYLATE COPOLYMER WITH NUCLIDE ACTIVATION AGENT AND/OR ANTI-CANCER COMPOUNDS

(75) Inventor: Bipin C. M. Patel, Hitchin (GB)

(73) Assignee: Psimei Pharmaceuticals PLC, Guildford (GB)

( * ) Notice: Subject to any disclaimer, the term of this patent is extended or adjusted under 35 U.S.C. 154(b) by 662 days.

(21) Appl. No.: 10/521,814

(22) PCT Filed: Jul. 4, 2003

(86) PCT No.: PCT/GB03/02919

§ 371 (c)(1),
(2), (4) Date: Aug. 11, 2006

(87) PCT Pub. No.: WO2004/009136

PCT Pub. Date: Jan. 29, 2004

(65) Prior Publication Data

US 2007/0258891 A1  Nov. 8, 2007

(30) Foreign Application Priority Data

Jul. 22, 2002  (EP) ................................. 02255107

(51) Int. Cl.
*A61M 36/14* (2006.01)
*A61K 51/00* (2006.01)
(52) U.S. Cl. .................... 424/1.81; 424/1.11; 424/1.65; 424/1.69; 424/9.1; 514/1; 514/2
(58) Field of Classification Search ................ 424/1.11, 424/1.65, 1.81, 1.85, 1.89, 9.1, 1.69; 514/1, 514/2, 5, 6, 9–19
See application file for complete search history.

(56) References Cited

U.S. PATENT DOCUMENTS

| 6,017,902 | A  | 1/2000 | Glass et al.    |
| 6,180,766 | B1 | 1/2001 | Schinazi et al. |
| 6,248,916 | B1 | 6/2001 | Kane et al.     |

OTHER PUBLICATIONS

Kasuya, et al., "Synthesis and characterization of HPMA copolymer-aminopropylgeldanamycin conjugates," Journal of Controlled Release, 2001, pp. 203-211, vol. 74. Elsevier Science Publishers B.V., Amsterdam, NL.

Kopeček, "Targetable Polymeric Anticancer Drugs," Annals New York Academy of Sciences, 1991, pp. 335-344.

Kopeček, "Water soluble polymers in tumor targeted delivery," Journal of Controlled Release, 2001, pp. 147-158, vol. 74. Elsevier Science Publishers B.V., Amsterdam, NL.

Minko, et al., "Efficacy of the Chemotherapeutic Action of HPMA Copolymer-Bound Doxorubicin in a Solid Tumor Model of Ovarian Carcinoma," Int. J. Cancer, 2000, pp. 108-117, vol. 86. Wiley-Liss, Inc.

Minko, et al., "HPMA copolymer bound adriamycin overcomes MDR1 gene encoded resistance in a human ovarian carcinoma cell line," Journal of Controlled Release, 1998, pp. 223-233, vol. 54. Elsevier Science Publishers B.V., Amsterdam, NL.

Novick et al., "Linklage of bornated polylysine to glycoside moieties of polyclonal antibody; boronated antibodies as potential delivery agents for neutron capture therapy," Nuclear Medicine and Biology, 2002, pp. 159-167, vol. 29. Elsevier Science Publishers B.V., Amsterdam, NL.

Olsson et al., "Uptake of a boronated epidermal growth factor-dextran conjugate in CHO xenografts with and without human EGF-receptor expression," Anti-Cancer Drug Design, 1998, pp. 279-289, vol. 13. Oxford University Press.

Sakuma, et al., "Biorecognizable HPMA copolymer-drug conjugates for colon-specific delivery of 9-aminocamptothecin," Journal of Controlled Release, 2001, pp. 365-379, vol. 75. Elsevier Science Publishers B.V., Amsterdam, NL.

Shiah, et al., "Biodistribution of free and N-(2-hydroxypropyl)methacrylamide copolymer-bound mesochlorin e6 and adriamycin in nude mice bearing human ovarian carcinoma OVCAR-3 xenografts," Journal of Controlled Release, 1999, pp. 145-157, vol. 61. Elsevier Science Publishers B.V., Amsterdam, NL.

Shiah, et al., "Combination chemotherapy and photodynamic therapy of targetable N-(2-hydroxypropyl) methacrylamide copolymer-doxorubicin/mesochlorin e6-OV-TL 16 antibody immunoconjugates," Journal of Controlled Release, 2001, pp. 249-253, vol. 74. Elsevier Science Publishers B.V., Amsterdam, NL.

Uhrich, Kathryn, "Hyperbranched Polymers for Drug Delivery," Trends in Polymer Science, Dec. 1, 1997, pp. 388-393, vol. 5, No. 12. Elsevier Science Publishers B.V., Amsterdam, NL.

Lu et al., "Design of novel bioconjugates for targeted drug delivery," Journal of Controlled Release, 2002, pp. 165-173, vol. 78. Elsevier Science Publishers B.V., Amsterdam, NL.

*Primary Examiner*—D L Jones
(74) *Attorney, Agent, or Firm*—Rothwell, Figg, Ernst & Manbeck

(57) ABSTRACT

The present invention relates to new anti-cancer compounds and in particular to new compounds for use in nuclide activation therapy, such as neutron capture therapy. Specifically this invention provides a conjugate having the general formula P-(L-NAT)$_n$ wherein P represents an N-hydroxypropylmethacrylamide-methacrylate copolymer having a molecular weight of 5-6,000 kDa; NAT represents a nuclide activation therapy agent; L represents a linker moiety capable of linking the polymer to the neutron capture therapy agent; and n represents an integer from 1-1,000.

14 Claims, No Drawings

CONJUGATES OF N-HYDROXYPROPYMETHACRYLAMIDE-METHACRYLATE COPOLYMER WITH NUCLIDE ACTIVATION AGENT AND/OR ANTI-CANCER COMPOUNDS

This application is a national filing under 35 USC 371 of PCT/GB2003/002919, filed Jul. 4, 2003 which claims priority from European Application 02255107.1, filed Jul. 22, 2002.

This invention relates to new anti-cancer compounds and in particular to new compounds for use in nuclide activation therapy, such as neutron capture therapy.

In nuclide activation therapy, a nuclide is activated and undergoes nuclear fission leading to the emission of highly ionizing radiation capable of destroying living cells. When the nuclide is activated using neutrons, the process is termed neutron capture therapy. The principle of neutron capture therapy (NCT) for the treatment for cancer was first described in 1936 by the American scientist Locker. In essence, when an NCT element, for example the stable nuclide boron-10, is irradiated by non-ionizing slow neutrons, a fission reaction results that leads to the emission of highly ionizing radiation with a range of 7 to 9 μm. In 1951 the first patient was treated and since then the principle has been successfully demonstrated in the clinic although thus far effective NCT drugs have been elusive.

Boron neutron capture therapy is a bimodal therapy requiring spatial and temporal overlap of neutrons and the drug. To achieve a biological effect, an interaction between slow neutrons and a boron carrying agent are necessary. The BNCT reaction of $^{10}B$ with neutrons may be summarised by the following equation:

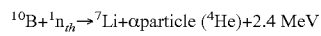

$$^{10}B + {}^1n_{th} \rightarrow {}^7Li + \alpha particle\ ({}^4He) + 2.4\ MeV$$

The 2.4 MeV energy is taken up as kinetic energy by the $Li^+$ and $He^{2+}$ ions. The two particles are sufficiently energetic to generate intense ionization tracks with a maximum range of 9 μm. Damage is thus confined to the diameter of a tumour cell, i.e. 10 μm. Accordingly, only the cells which contain $^{10}B$ are damaged, while non-$^{10}B$ containing (healthy) cells are left intact. The $^{10}B$ nuclide is stable and non-radioactive and its nucleus has a very large neutron absorption cross section for slow neutrons, i.e. 2700 times greater than hydrogen. This translates into an ability to absorb neutrons of several thousand times better than that of the elements constituting living tissues, such as hydrogen, oxygen and carbon.

BNCT can be used to treat cancers which are normally treated with radiotherapy, such as lymphomas and skin cancers, as well as cancers of the brain, breast, lung, head and neck, bone, prostate, pancreas and cervix. In addition, when surgical removal of a tumour is planned, BNCT may also be used to help reduce the size of the tumour and to reduce the associated normal tissue loss.

BNCT has been driven by the potential benefits of selective "in situ" radiotherapy and as a potential substitute to conventional X-ray radiotherapy. Over 500 patients have received experimental BNCT treatment for brain and skin tumours world wide. Predominnantly, two experimental compounds 4-dihydroxyborylphenylalanine (BPA) and sodium mnercaptoundecahydrododecaborate (BSH) have been used in the clinical trials.

In conventional radiotherapy the biological effect is spread over the entire irradiated area whilst with BNCT it is specific to those cells containing $^{10}B$ carrier molecules. A relatively high radiation dose is required with radiotherapy to generate the destructive ionization tracks for the biological effect. This is a limiting factor in the effectiveness of the treatment. Radiotherapy is limited by the inherent nature -of the low LET (linear energy transfer) radiation beam which comprise of electrons (β-particles) or photons (X-rays and γ-rays). With BNCT short range high energy α and $^7Li$ particles are generated. These particles are high LET particles that are intensely ionizing and exhibit a greater more potent destructive propensity. Hence, the BNCT dose required to generate an equivalent radiotherapy biological effect is very much smaller than the relative radiotherapy dose.

Thus, in contrast to radiotherapy, BNCT offers target tissue selectivity via the specificity of the drug. Lethal radiation is only generated where $^{10}B$ is localised, i.e. within the tumour tissue. The course of treatment can be completed within 2-4 days. Slow neutrons are non-ionizing. Also BNCT is capable of destroying diff-use tumours which are normally not clearly demarcated.

BNCT is not dependent upon oxygen levels in the tumour as many are hypoxic and can also be used where the cancer treatment is anatomically compromised. Deep-seated tumours can be treated at anything from 4-8 cm depth and beyond.

BNCT is less demanding for the patient than conventional radiotherapy as it can be given several times over a period of 2-4 days while in contrast conventional radiotherapy needs to be given up to 30 times over a period of six weeks.

In such a binary system, each component may be manipulated independently of the other. The interval between administration of the $^{10}B$ agent and neutron irradiation may be adjusted to an optimum time to provide the highest differential $^{10}B$ concentrations between normal tissues and the tumour tissue. Similarly, the neutron beam may be collimated so that the field of irradiation is limited to the tumour site and normal tissues having some residual $^{10}B$ concentration may be excluded from the treatment volumes.

However to obtain the potential benefits of NCT as an "in situ" cellular radiotherapy, there are a number of prerequisites. The neutrons must be of an energy range where only the NCT nuclides, for example the $^{10}B$ atoms, are able to undergo a fission reaction. The NCT agent must also be selectively localised in the target tissue. For example, 15-35 μg/g of tumour tissue (equating to $10^9$ boron atoms) is widely quoted to be the amount of $^{10}B$ necessary for effective BNCT using a neutron beam from a nuclear reactor of fluence $10^9$ neutrons per second per $cm^2$.

However, large concentrations of the boron-containing drugs need to be administered to achieve the $10^9$ boron atoms' per tumour cell. To illustrate this point, Table 1 below summarises three BNCT compounds that have been the subject of much preclinical and clinical research. BPA and BSH are in clinical use and the third is an experimental compound in preclinical development.

TABLE 1

| Compound | Absolute tumour concentration (µg/g) | Tumour:blood Ratio | Tumour:CNS ratio | Dose |
|---|---|---|---|---|
| BPA (in clinical trials) | 16.5 | 2.2:1.0 | 1.7:1.0 | 900-1200 mg/kg (30 mg/ml) |
| BSH (in clinical trials) | 6.9 | 0.7:1.0 | 3.0:1.0 | — |
| CuTCPH (precluded development) | 114.0 | 570:1.0 | 57:1.0 | 200 mg/kg (6 mg/ml) |

However, the above compounds need to be administered in extremely high concentrations for example up to 1200 mg per kg for BPA in a 30 mg/ml intravenous solution. This is a major concern and a disadvantage for the ill patient as there is a need to administer several litres of drug within a few hours to achieve the meager tumour to blood differential of 3:1. As a result patients are exposed to cardiovascular shock. To achieve this tumour to blood differential infusion protocols of 1, 2, 4, 6 and 8 hours are necessary. Also BPA and BSH have no selectivity for tumours. CuTCHP has higher tumour to blood ratios but suffers from the need to administer a 200 mg/kg dose which again is extremely high and would require about 15 g of compound in 100-1000 mL of liquid. New compounds are clearly required that overcome these shortcomings. However, after over 50 years of research and development effort, only two sub-optimal compounds (BPA and BSH) have entered clinical trials.

Accordingly, the present invention provides a conjugate having the general formula

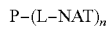

P–(L–NAT)$_n$ wherein

P represents an N-hydroxypropylmethacrylamide-methacrylate copolymer having a molecular weight of 5-6,000 kDa;

NAT represents a nuclide activation therapy agent;

L represents a linker moiety capable of linking the polymer to the neutron capture therapy agent; and n represents an integer from 1-1,000.

The present invention thus provides a conjugate with improved tumour targeting compared to previously available compounds.

The present invention also provides a pharmaceutical composition containing the conjugate as defined above.

The present invention further provides the use of the conjugate as defined above for the preparation of a medicament for the treatment of cancer, as well as the use of the conjugate as defined above for the treatment of cancer. Preferably the invention relates to the treatment of solid tumours, such as brain, breast, head and neck, prostate, lung, bone, pancreas and liver, and colon cancers. In addition, the present invention provides a method for treating cancer comprising administering a conjugate as defined above to a patient followed by activating the NAT agent at the site of the tumour.

The compounds of the present invention are large molecules dissolved in an aqueous medium suitable for parenteral administration. The polymer-NAT conjugates have molecular weights in excess of 5 kDa compared with conventional drugs of 200-500 Da These compounds on their own do not have any anti-tumour activity but in the presence of an activation source, e.g. neutrons, the NAT reaction takes place to generate the toxic high LET particles (a particles and lithium ions).

The polymer-NAT conjugates contain three components, namely a polymer, an NAT agent and a linker.

The polymer is a biocompatible (e.g. non-immunogenic and non-thrombotic, i.e. does not interfere with platelets and clotting factors), typically water soluble natural or synthetic polymer. The conjugate has a water solubility greater than 0.1 mg/ml, more preferably 1-100 mg/ml, most preferably 10-50 mg/ml. The polymer is pharmaceutically inert.

The polymers are required to have a blood-plasma half-life of 0.1 to 24 hours, preferably 0.2 to 12 hours, particularly preferably 1-6 hours. Sufficient half-life is required for the molecules to enter a cell via pinocytosis. Pinocytosis is a slow process whereby extracellular fluid (containing the drug molecule) is taken into the cytoplasm.

The molecular weight and shape of the molecule (e.g. string or a globule) will determine the filtration rate out of the kidney. The molecular weight of the polymer is 5-6,000 kDa, preferably 5-100, more preferably 10-70, more preferably 15-45, most preferably 20-40 kDa.

The polymer is water-soluble, preferably with a water solubility greater than 0.1 mg/ml, more preferably 50 mg/ml, most preferably greater than 100 mg/ml. These solubilities are necessary so when the NAT active agent (these normally have a poor water solubility) is conjugated the overall effect on the solubility of the compound is normally negligible. Water solubility also allows a significant decease in the volume of drug solution which needs to be administered to the patient. It also negates the requirement of potentially toxic co-solvents in drug formulations.

However, low water solubility polymers are also useful (solubility below 0.1 mg/ml) but require the use of pharmaceutical excipients, such as oils, surfactants and/or emulsifiers, to generate a sufficiently concentrated liquid injectable system.

The polymer may be modified by introducing amino acids or artificial sugars which do not undergo enzymatic degradation, in order to enhance the stability of the polymer and increase the half-life.

The amount of the two monomers in the copolymer may be varied. The ratio of hydroxypropylmethacrylamide to methacrylate is preferably from 100:1 to 1:1, most preferably 20:1 to 1:1.

The NAT active nuclide must be capable of undergoing nuclear fission to produce particles which are sufficiently energetic to destroy tumour cells but which confine the cell damage to the diameter of a tumour cell, i.e. 10 µm. Such nuclides are known in the art and are exemplified by $^{6}$Li, $^{10}$B, $^{22}$Na, $^{58}$Co, $^{113}$Cd, $^{126}$I, $^{135}$Xe, $^{148m}$Pm, $^{149}$Sm, $^{151}$Eu, $^{155}$Gd, $^{157}$Gd, $^{164}$Dy, $^{184}$Os, $^{199}$Hg, $^{230}$Pa, $^{235}$U and $^{241}$Pu. More preferably the nuclide is $^{6}$Li, $^{10}$B, $^{22}$Na, $^{58}$Co, $^{113}$Cd, $^{126}$I, $^{135}$Xe, $^{148m}$Pm, $^{149}$Sm, $^{151}$Eu, $^{155}$Gd, $^{157}$Gd, $^{164}$Dy or $^{184}$Os. Typically, the particular element is enriched with the NAT active nuclide. The NAT active nuclides are attached to the polymer via compounds which carry the NAT active nuclide. These compounds are known in the art and are exemplified below:

Boronated amino acids and peptides, e.g. boronophenylalanine (BPA), see Soloway Chem. Rev. (1998) Vol 98, No. 4, pages 1531-1534 and Snyder, H R et al J. Am. Chem. Soc. (1958) 80, 835;

Modified carborane cages, such as $[B_{10}H_{10}]^{2-}$ (decahydrodecaborate) and $[B_{12}H_{12}]^{2-}$ (dodecahydrododecaborate), e.g. $C_2B_{12}H_{12}$, see Hawthorn, M F et al J. Am. Chem. Soc. (1959) 81, 5519 and Grimes, R. N. in "Carboranes" Academic Press NY (1970); Mercaptoborates, such as mercaptoundecahydrododecaborate ($B_{12}H_{11}SH^{2-}$)(BSH), the structure of the disodium salt is shown below, which may also be in the form or a dimer (BSSB), see Soloway, A. H. et al J. Med. Chem. (1967) 10, 714;

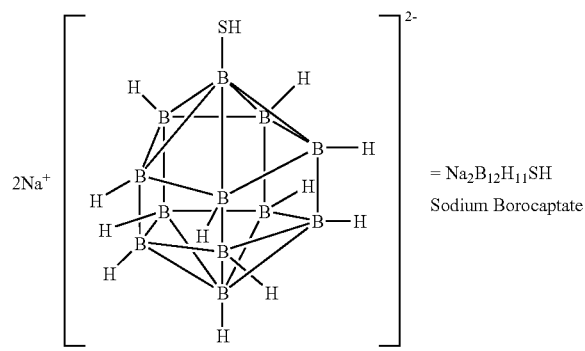

Porphyrins and phthalocyanines, e.g. BOPP and LTCPs (NiTCP, CUTCP, NiTCPH and CuTCPH) in which the porphyrins carry four carborane cages, see Ozawa, T. Pro. Am. Ass. for Cancer March 1998, 39, p586 and Miura, M., Radiation Research (2001) 155, 603-610 (see structures below);

Boron-containing nucleic acid precursors, such as boronated and carborane-containing pyrimidines and purines, e.g. 5-(dihydroxyboryl) uracil, 5-carboranyluracil, see Liao, T. K J. Am. Chem. Soc. (1964) 86, 1869, Schinazi, R. F. J. Org. Chem. Soc. (1985) 50, 841, and Nemoto, H. J. Chem. Soc. Chem. Commun. (1994) 577; and Foliates, growth factors, hormones, radiation sensitisers, phosphates, phosphonates and phosphoramidates, cyclic thiourea derivatives, amines, promazines, hydantoins, barbiturates, see Soloway Chem. Rev. (1998) Vol 98, No.4, pages 1545-1550.

Structure of various lipophilic carboranyltetraphenylporphyrins.

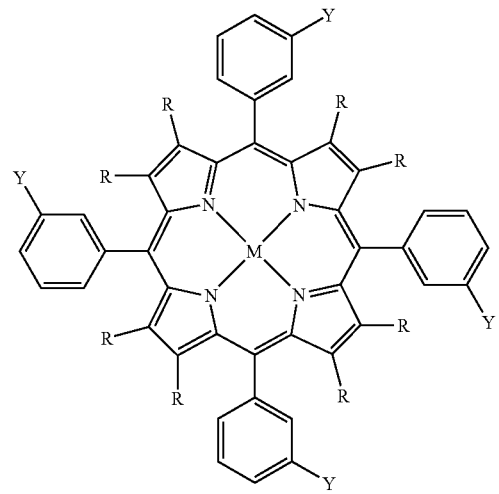

NiTCP, R = CH$_2$CO$_2$CH$_3$, M = Ni
CuTCP, R = CH$_2$CO$_2$CH$_3$, M = Cu
NiTCPH, R = H, M = Ni
CuTCPH, R = H, M = Cu

Y =

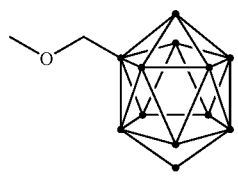

R may also represent halogen, preferably Br or Cl, or a nitro group (NO).

Other nuclides may be incorporated in the same manner. For example, a combined BNCT and GdNCT compound where the Gd nuclide and a carborane cage are on the same molecule is known in the art, see Soloway (1998) Chem. Rev. Vol 98, No. 4, page 1519.

The NAT agent should preferably make up 1-30%, preferably 5-10% of the overall mass of the polymer-NAT conjugate.

The NAT agent is activated using known techniques, such as irradiation with electromagnetic radiation (e.g. X-rays, light, microwaves, gamma rays) or by-neutrons or by ultrasound, protons, carbon ions, pion therapy, electron beam therapy, antiproton therapy, photon therapy, photodynamic therapy. In the case of neutrons, the technique is termed neutron capture therapy and the agent is termed a neutron capture therapy (NCT) agent.

The linker may be any group which links the polymer and the NCT agent and which does not effect the in vivo solubility or toxicity properties of the polymer-NAT conjugate. Such linkers include linear or branched $C_{1-15}$ alkyl which may be saturated or unsaturated, optionally substituted by carbonyl, amide, hydroxyl or halogen, such as methyl, ethyl, propyl, n-butyl, i-butyl, t-butyl, 1-methylbutyl and methylpentyl; and peptides, preferably 1-10 amino acids in length in which the amino acids may be further substituted with amino, thio, carboxyl, carboxamide or imidazole groups. Preferred peptides are Gly-Gly [SEQ ID NO: 1], Gly-Phe-Gly [SEQ ID NO: 2], Gly-Phe-Phe [SEQ ID NO: 3], Gly-Leu-Gly [SEQ ID NO: 4], Gly-Val-Ala [SEQ ID NO: 5], Gly-Phe-Ala [SEQ ID NO: 6], Gly-Leu-Phe [SEQ ID NO: 7], Gly-Leu-Ala [SEQ ID NO:8], Ala-Val-Ala [SEQ ID NO: 9], Gly-Phe-Leu-Gly [SEQ ID NO: 10], Gly-Phe-Phe-Leu [SEQ ID NO: 11], Gly-Leu-Leu-Gly [SEQ ID NO: 12], Gly-Phe-Tyr-Ala [SEQ ID NO: 13], Gly-Phe-Gly-Phe [SEQ ID NO: 14], Ala-Gly-Val-Phe [SEQ ID NO: 15], Gly-Phe-Phe-Gly [SEQ ID NO: 16], Gly-Phe-Leu-Gly-Phe [SEQ ID NO: 17] and Gly-Gly-Phe-Leu-Gly-Phe [SEQ ID NO: 18]. Particularly preferred peptides are Gly-Gly [SEQ ID NO: 1] and Gly-Phe-Leu-Gly [SEQ ID NO: 10].

Some of the peptide linkers may be degraded by lisosomal enzymes so that the NAT compound is released within the tumour cell.

The linker is attached to the polymer and the NAT agent by conventional synthetic methods well known to the skilled person. The following bonds provide a suitable means for attaching the NAT agents to the polymer an amide bond, an ester bond, a hydrazide bond, a urethane (carbamate) bond, a carbonate bond, an imine (Schiff base) bond, a thioether bond, an azo bond or a carbon-carbon bond. Alternatively, the NAT agent may be attached directly to the polymer itself, i.e. the linker is a covalent bond.

Amide bonds may be made using an amino group ($-NH_2$) and a carboxylic acid group (COOH). The latter should be transformed to a more reactive intermediate such as an acid chloride (COCl) or using coupling agents such as carbonyl diimidazole (CDI) or *dicyclohexylcarbodiimide (DCC). Other substrates for the amino group are acid anhydrides and esters. Ester bonds may be made from hydroxyl groups (OH) and the activated carboxylic acids mentioned above and acid anhydrides. Hydrazide bonds may be made from acyl halides (such as the acid chloride above) and a hydrazine ($NH_2NHR$). Carbamate bonds may be made from phosgene (ClCOCl) or, preferably, trichloromethyl chloroformate ($CCl_3OCOCl$), which may be treated with an alcohol and an amine. Carbonate bonds may also be made from phosgene or trichloromethyl chloroformate, which may be treated with two alcohol groups. Imines (or Schiff bases) may be made by condensation between an aldehyde (RCHO) or ketone (RCOR) and an amine. Aldehydes are easily made by oxidation of primary alcohols and ketones may be made by oxidation of secondary alcohols. Thioethers may be made by first converting a group such as an alcohol, into a good leaving group, such as a tosylate, mesylate, triflate or halide, and treating it with a mercaptide ($RS^-$), which substitutes the leaving group with RS. See, for example, Schacht E (1987) in: Illum L, Davis S S (eds) "Polymers in drug delivery", Wright, Bristol, p131.

Typically, the linker is attached to the polymer at the methacrylate monomers, preferably via an amide bond Methacrylate monomers which do not have pendant NAT agents (or any other pharmaceutically active agent) may still have a linker which may be capped using a capping compound, for example 2-amino-1-propanol.

For effective therapy planning and BNCT dose calculations, it is important to know the location and concentration of the drug in the tumour. Therefore, in the clinical setting as part of the treatment planning it is important to know the site and the amount of the NAT agent in the tumour mass in order to calculate the clinical neutron dose. For example, a macromolecule may carry a metal which can be imaged using diagnostic techniques, such as PET, SPECT, MRI. The lipophilic carboranyltetraphenylporphyrins (LCTP), for example, are able to carry a metal ion. Such a metal may be selected from vanadium (V), manganese (Mn), iron (Fe), ruthenium (Ru), technetium (Tc), chromium (Cr), platinum (Pt), cobalt (Co), nickel (Ni), copper (Cu), zinc (Zn), germanium (Ge), indium (In), tin (Sn), yttrium (Y), gold (Au), barium (Ba), tungsten (W), gadolinium (Gd) and gallium (Ga). The most preferred metals are Cu and Ni.

Positron Emission Tomography (PET) may also be used to provide an indication of the position and concentration of the polymer-NAT conjugate in the tumour. In PET, radio nuclides such as $^{18}F$ (half-life of about 2 hours) or $^{11}C$ (half-life of 20 minutes) are preferred. A single fluorine atom may be incorporated into the polymer backbone or ideally in an amino acid, preferably Phe, in the linker chain. This provides a very powerful tool for diagnosis and treatment planning enabling customised individual polymer-NAT conjugate drug dosing. The presence of a fluorine atom provides a means of substituting the F for the radionuclide $^{18}F$ at the time of diagnosis using well known PET imaging chemistry.

Some preferred examples of polymer-NAT conjugates of the present invention will now be described.

Preferably, the polymer is a copolymer of N-(2-hydroxypropyl)methacrylamide (HPMA) and methacrylic acid; the linker is a peptide, such as Gly-Phe-Leu-Gly [SEQ ID NO: 10]; and the NAT agent is selected from o-carboranylalanine $B_{10}C_2H_2$—$CH_2CHCO_2NH_2$, carborane butamine $B_{10}C_2H_2$—$(CH_2)_3CHCO_2NH_2$, BPA (p-boronophenylalanine), $B_{12}H_{11}SH$ (BSH) (mercaptoundecahydrododecacarborate), boronated porphyrins, BSH-glutathione disulfide, and water soluble tetracarbonylphenylporphyrin eg. NiTCP.

Particularly preferred conjugates are:

| | |
|---|---|
| HPMA-co-MA-Gly-Phe-Leu-Gly-BSH | [SEQ ID NO: 10] |
| HPMA-co-MA-Gly-BPA-Leu-Gly-BPA | [SEQ ID NO: 10] |
| HPMA-co-MA-Gly-BPA-Leu-Gly-Gly-BPA | [SEQ ID NO: 19] |
| HPMA-co-MA-Gly-Phe-Leu-Gly-Carborane butamine ($B_{10}C_2H_{11}(CH_2)_3CHCO_2NH_2$) | [SEQ ID NO: 10] |
| HPMA-co-MA-Gly-BPA-Leu-Gly-Carborane butamine ($B_{10}C_2H_{11}-(CH_2)_3CHCO_2NH_2$) | [SEQ ID NO: 10] |
| HPMA-co-MA-Gly-Phe-Leu Gly-CuTCPH | [SEQ ID NO: 10] |
| HPMA-co-MA-Gly-Phe-Leu-Gly-CuTCPHBr | [SEQ ID NO: 10] |

The polymer-NAT conjugates of the present invention are selectively targeted to tumours and exploit a number of tumour properties. For example, the tumour has a negative osmotic pressure since there is no lymphatic drainage, leading to trapping of the polymer-NAT conjugate (the so-called Enhanced Permeability Retention (EPR) effect). The vast majority of small compounds thus enter into the tumour via diffusion and tend to remain in the turnout bed and move between the cells through gap junctions. The compounds normally enter the cells by endocytosis into the cytoplasm and end up in the lysosomal compartment. The polymer-NAT conjugates are targeted to the cell membrane, the cytoplasmic organelle, e.g. mitochondria, endothelial reticule or Golgi apparatus, and/or the nucleus. The polymer-NAT conjugate being nearer to the nucleus and cellular organelles increases the probability of irreversible DNA or cellular damage from the ionising particles (e.g. a and Li ion) resulting from the fission of the NAT agent.

The polymer component of the polymer-NAT conjugate may also be modified to target particular areas of the body. For example, the asialoglycoprotein receptor on hepatocytes can recognise both galactose and N-acetylgalactosamine. Accordingly, incorporating these components into the polymer allows polymer-NAT conjugate of the present invention to be directed to the liver.

Galactose may be incorporated in to the monomer of the HPMA with a protected hydroxyl group. For example, 1,2,3,4-di-O-isopropylidene-6-O-methacryloyl-α-D-galactopyranose is synthesised and then copolymerised with HPMA followed by removing the protecting group, isopropylidene, with formic acid. See, Chytry, V. et al New Polymer Material (1987) 1, 21. N-acylated galactosamine is attached using the reactive HPMA copolymer precursor having side chains terminated with p-nitropyridine so esters. These are aminolyzed with galactosamine in DMSO at room temperature and pressure.

In addition, the non-specific uptake of the polymer-NAT conjugate may be enhanced by incorporating a positive charge (e.g. using methacryloxylethyltrimethylammonium chloride) or hydrophobic comonomers (e.g. using N-[2-(4hydroxyphenylethyl)]acrylamide or N-methacryloyltyrosinamide) into the polymer.

NAT requires that a polymer-NAT conjugate is administered at a dose of 0.1-100 mg/kg body weight, preferably 0.1-50 mg/kg, particularly preferably 1-30 mg/kg. The dose should deliver at least 10 μg/g of active nuclide, e.g. $^{10}$B atoms, per gram of wet tumour tissue, preferably at least 25 μg/g, more preferably at least 80 μg/g, more preferably at least 160 μg/g and most preferably over 200 μg/g.

Incidentally, the polymer-NAT conjugate of the present invention provides a significant reduction in systemic toxicity compared to known NAT agents and hence a higher dose may be given leading to a greater concentration of the NAT agent inside the tumour cell. Toxicity is reduced since the NAT agent within the polymer-NAT conjugate is not available for interaction with the biological environment. In addition, since the polymer-NAT conjugate is retained by the tumour for long periods of time, i.e. several hours to days, there is no need for multiple dosing thereby widening the clinical treatment window, In addition to the NAT agent, other drugs, or their prospective prodrugs, may be incorporated into the polymer-NAT agent of the present invention thereby providing increased anti-cancer activity. That is, a polymer-NAT conjugate having the general formula P-(L-NAT)$_n$(L-chemotheraptuic agent)$_m$ wherein P, L, NAT and n have the same meaning as defined above, L may be the same or-different and m is an integer from 1-1000, preferably 1-500, more preferably 1-100, most preferably 1-20. Such chemotherapeutic agents may include, for example, any one of the following: 5-(azurudub-1-yl)-4-dihydroxylamino-2-nitrobenzamide, phenylenediamine mustard, benzoic acid mustards, ganciclovir triphosphate, adenine arabinonucleoside triphosphate (araATP), hydrogen peroxide, cyanide, superoxide, methotrexate, mitomycin alcohol, etoposide, palytoxion, melphalan, 5-(aziridin-1-yl)-4-hydroxylamino-2-nitrobenzamide, actinomycin D, mitomycin C, taxanes, such as taxol and taxotere, topoisomerage inhibitors, such as camptothecin and topotecancyclophosphamide, carmusline, 5-fluorouracil, cytrabine, mercaptopurine, anthracyclines, daunorubicin, doxorubicin, epirubicin, vinca alkaloids, vinblastin, vincristine, dactinomycin, mitomycin C, lasparaginase, G-CSF, cisplatin and carboplatin.

A preferred conjugate of this type is HPMA-co-MA-[Gly-Phe-Leu-Gly-BSH)(Gly-Phe-Leu-Gly-Y)], where Y is the anticancer agent [SEQ ID NO: 20], for example:

[SEQ ID NO: 20]
HPMA-co-MA [(Gly-Phe-Leu-Gly-BSH)(Gly-Phe-Leu-Gly

Doxorubicin)]

[SEQ ID NO: 20]
HPMA-co-MA [(Gly-Phe-Leu-Gly-BSH)(Gly-Phe-Leu-Gly

Ellipticin)]

[SEQ ID NO: 20]
HPMA-co-MA [Gly-Phe-Leu-Gly-BSH)(Gly-Phe-Leu-Gly

Cisplatin)]

A feature of the polymer-NAT conjugates of the present invention is that they build up in a tumour without the need for a targeting moiety attached to the polymer. However, the polymer-NAT conjugate, with or without an active anti-cancer chemotherapeutic agent, may contain a targeting moiety attached to the polymer. These targeting moieties are selected to increase the concentration of the compound at the desired target tissue. Such moieties significantly change the biodistribution of the conjugate by providing a means of selectivity. Such targeting moieties include (N-acylated) galactosamine, (6-O-bound) galactose, (N-acylated) fucosylamine, melanocyte stimulating hormone, and secretin.

The present invention will now be illustrated by a number of examples which describe a new class of polymer-NAT conjugates which overcome the shortcomings of current BNCT agents.

EXAMPLES

Polymers were obtained from Polymer Laboratories Ltd. The certificates of analysis were obtained from Butterworth.

In examples 1 and 2 below, reaction of 4-boronophenylalanine (BPA:) with the p-nitrophenyl ester group of the polymer leads to the formation of a boron-containing polymer with the displacement of p-nitrophenol as depicted by the reaction scheme below.

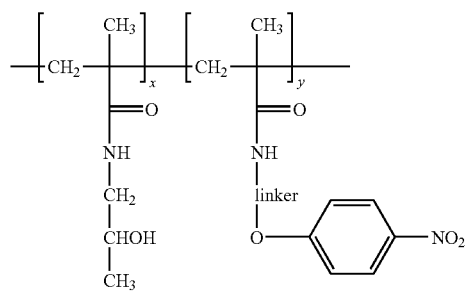
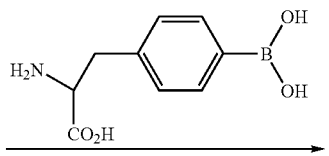

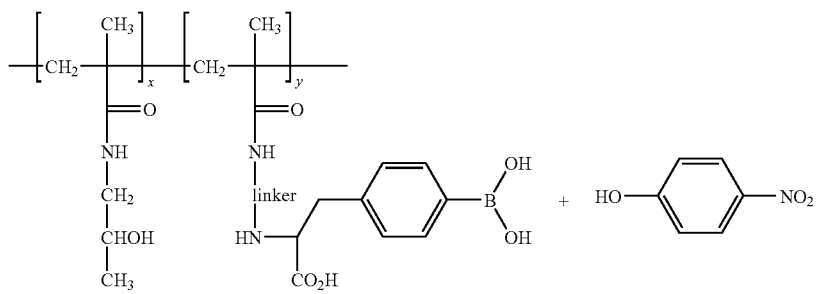

Commercially available poly(HPMA-co-MA-GG-ONp) from Polymer Laboratories Ltd has an average molecular weight of 28,100 with a broad molecular weight distribution, weight average molecular weight/number average molecular weight, $M_w/M_n=1.31$, leading to average values of x=153, y=17 (MW=27,624). Poly(HPMA-co-MA-GFLG-ONp) has an average molecular weight of 47,200 ($M_w/M_n=1.53$). From the average molecular weight, average values of x and y may be calculated as x=225, y=25 (MW=47,131). These values have been used to calculate how much of the boron substituted phenylalanine should be added.

Example 1

Gram-scale preparation of poly(HPMA-co-MA-GG-F[4-B(OH)$_2$])

Powdered poly(HPMA-co-MA-GG-ONp) (1.1 g, 40.0 μmol) and 4-boronophmnylalanine ($^{10}$B enriched) (0.15 g, 740 μmol) were placed in a dried flask which was sealed with a septum and flushed with argon. Anhydrous DMSO-(11 mL) was added and the mixture was stirred until all the material had dissolved to produce a cloudy solution. Triethylamine (4 drops) as a catalyst was added causing the solution to become yellow. The,solution was stirred at 20-22° C. (oil bath temperature) overnight under argon. The solution was diluted with diethyl ether (200 mL) and the solvent was decanted off leaving a solid sticky precipitate. The solid sticky precipitate was triturated with further portions of diethyl ether until it was no longer sticky. Residual solvent was evaporated in vacuo (ca 0.4 mmHg) at 36° C. for 3 h. The product poly (HPMA-co-MA-GG-F[4-B(OH)$_2$]) was obtained as a beige/yellowish solid (1.20 g, 104%), $^1$H NMR analysis revealed the presence of some residual diethyl ether and DMSO.

Boron analysis was done by Butterworth Laboratories Ltd. It was found that boron content of the poly(HPMA-co-MA-GG-F[4-B(OH)$_2$]) was 0.47% (the expected was 0.59%). The low values could be due to incomplete reaction of the polymer with 4-boronophenylalanine and the presence of residual solvent.

Example 2

Gram-scale preparation of poly(HPMA-co-MA-GFLG-F[4-B(OH)$_2$])

Powdered poly(HPMA-co-MA-GFLG-ONp) (1.1 g, 23.3 μmol) and 4-boronophenylalanine ($^{10}$B enriched) (0.13 g, 625 μmol) were placed in a dried flask which was sealed with a septum and flushed with argon Anhydrous DMSO (11 mL) was added and the mixture was stirred until all the material had dissolved to produce a cloudy solution. Triethylamine (4 drops) as a catalyst was added causing the solution to become yellow. The solution was stirred at 20-22° C. (oil bath temperature) overnight under argon. The solution was diluted with diethyl ether (200 mL) and the solvent was decanted off leaving a sticky precipitate. The sticky precipitate was triturated with further portions of diethyl ether until it was no longer sticky. Residual solvent was evaporated in vacuo (ca 0.4 mmHg) at 36° C. for 3 h. The final product poly(BPMA-co-MA-GFLG-F[4-B(OH)$_2$]) was obtained as a beige/yellowish solid (1.23 g, 102%), $^1$H NMR analysis revealed the presence of some residual diethyl ether and DMSO.

Boron analysis was done by Butterworth Laboratories Ltd. It found that the polymer contains 0.40% boron (the expected was 0.48%). These slightly low values could-be due to incomplete reaction of the polymer with 4boronophenylalanine and the presence of is residual solvent.

The chemical structures of the polymer-NAT conjugates prepared in examples 1 and 2 are:

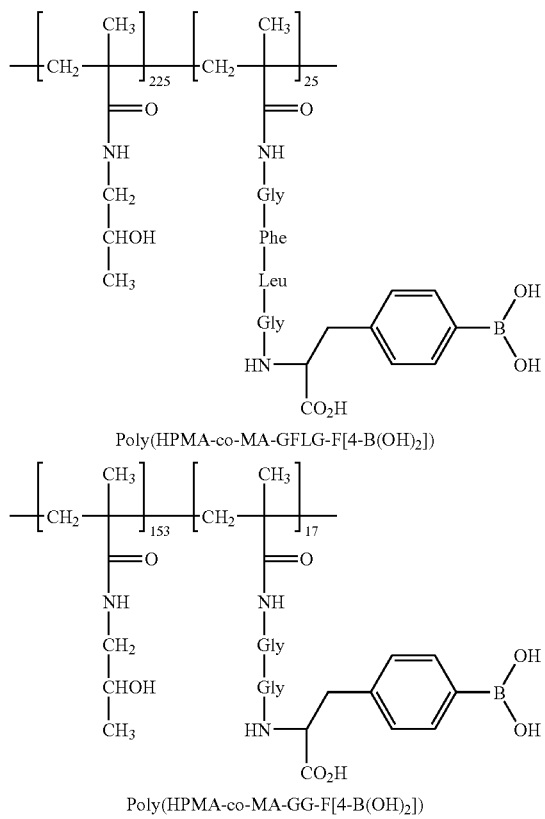

Poly(HPMA-co-MA-GFLG-F[4-B(OH)2])

Poly(HPMA-co-MA-GG-F[4-B(OH)2])

The polymer-NAT conjugates of examples 1 and 2 only differ in their peptide linkers. The polymer-NAT conjugate of example 1 has the peptide linker Gly-Phe-Leu-Gly [SEQ ID NO: 10] which is enzymatically degraded in the lisosomal compartment of a cell to release the BPA whereas the polymer-NAT conjugate of example 2 has the peptide linker "Gly-Gly" [SEQ ID NO: 1] which is not degraded leaving the entire molecule intact. The biodegradable polymer is able to release the boron-carrying molecule into the cytoplasm and has the opportunity to diffuse into the heart of cellular organelles and most importantly into the nucleus. In BNAT, the closer the boron carrier molecule is to the DNA-the, more effective the cell kill. However, with the non-degradeable polymer-NAT conjugate, the molecule remains intact and is unable to leave the cell once it has been internalised. This allows a build up of a very high concentration of the boronated ploymer in a cell via- multiple doses which otherwise may not be possible due to systemic toxicity of the boronated polymer.

Example 3

Preperation of poly(HPMA-co-MA-GG-F BSMel) (Applicant's code PP403)

The poly (HPMA-co-MA-GG-F BSMel) was synthesised using commercially available sodium borocaptate. The sodium borocaptate was first converted to a phenylalanine derivative, sodium boronocaptate melphalan (BSMel) in "Step 1" using the procedure discribed in U.S. Pat. No. 6,017, 902. This step was followed by "Step 2" in which BSMel was reacted with poly(HPMA-co-MA-GG-ONp) to yield the poly (BPMA-co-MA-GG-F BSMel).

Step 1 Preparation of BSMel

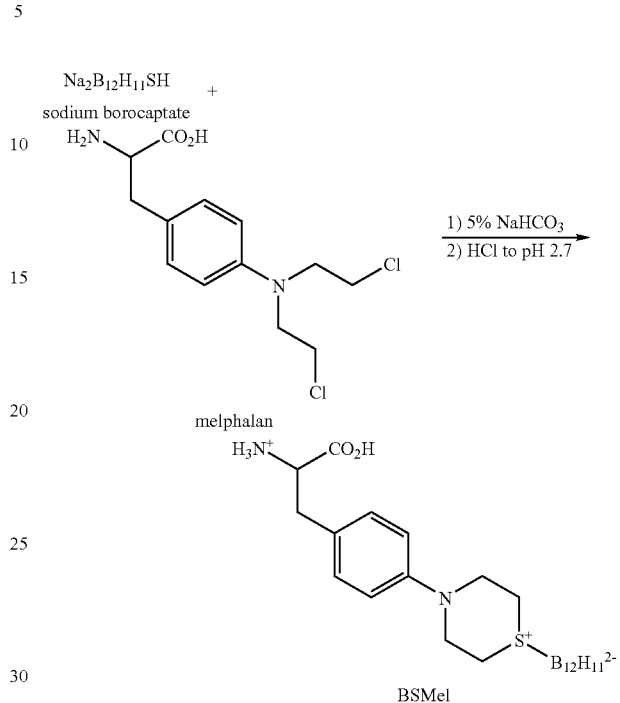

BSMel

Sodium borocaptate (0.95 g, 4.32 mmol) was dissolved in a 5% sodium hydrogen carbonate solution (30 mL). Melphalan, a yellowish solid, (0.22 g, 0.72 mmol) was added and the suspension was stirred at room temperature over a 48 h. The yellowish solid melphalan dissolved completely and a fine white precipitate was formed. The mixture was chilled (ca 4° C.) for 3 h and then filtered through a nylon membrane. The resultant solid was dissolved in water (30 mL) with heating (ca 100° C. bath temperature). The resultant solution was allowed to cool to room temperature and was filtered. The pH of the solution was adjusted to 2.7 by careful dropwise addition of conc. hydrochloric acid causing the precipitation of a fine solid. After chilling overnight (ca 4° C.), the product was collected by filtration and washed with cold water. Residual solvent was evaporated in vacuo (ca 0.4 mmHg) at ca 30° C. for 5 h. The product was obtained as a light tan solid (0.19 g, 65%).

Step 2 Preparation of BSMel Polymer

Powdered poly(HPMA-co-MA-GG-ONp) (1.1 g, 40.0 μmol) was placed in a dried flask which was sealed with a septum and flushed with argon. Anhydrous DMSO (11 mL) was added and the mixture was stirred until all the material had dissolved. BSMel (0.069 g, 169 μmol) from Step 1 was added. When all the solid had dissolved, triethylamine (2 drops) was added causing the solution to become yellow. The solution was stirred at 20-22° C. (oil bath temperature) overnight under argon. 3-Amino-1-propanol (41 μl, 536 μmol) was added and the solution was stirred for a further 3 h. The solution was diluted with diethyl ether (200 mL) and the solvent was decanted off leaving a sticky precipitate. The yellow solid was triturated with further portions of diethyl ether until it was no longer sticky. Residual solvent was evaporated in vacuo. Yield 1.10 g.

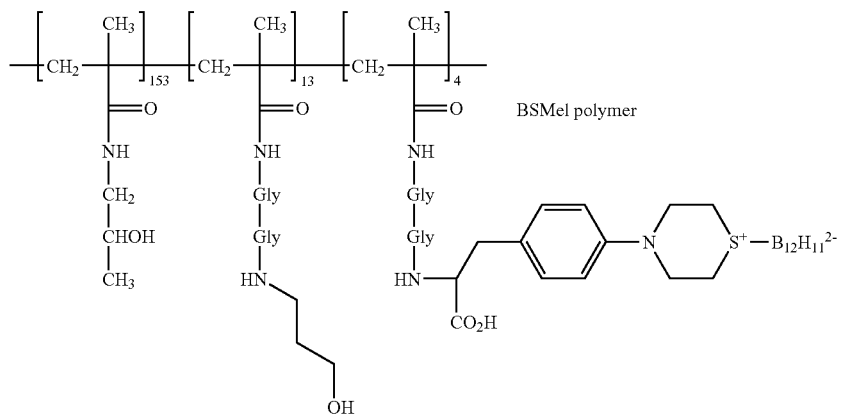

This non-biodegradable boron-carrying polymer is able to deliver 12 boron atoms per boron carrier and there are between 3-4 BSMel molecules per. polymer molecule. Therefore, the BSMel polymer is able to deliver in excess of 30-40 times more boron per polymer molecule than those in Examples 1 and 2. This provides a very powerful way of delivering a high concentration of boron with a compartively low concentration of polymer.

Example 4

Preperation of poly(HPMA-co-MA-GFLG-BSMel) (PP404)

Powdered poly(HPMA-co-MA-GFLG-ONp) (1.1 g, 23.3 µmol) was placed in a dried flask which was sealed with a septum and flushed out with argon. Anhydrous DMSO (11 mL) was added and the mixture was stirred until all the material had dissolved. BSMel (0.062 g, 152 µmol) was added. When all the solid had dissolved, triethylamine (2 drops) was added causing the solution to become yellow. The solution was stirred at 20-22° C. (oil bath temperature) overnight under argon. 3-Amino-1-propanol (35 µL, 456 µmol) was added and the solution was stirred for a further 24 h. The solution was diluted with diethyl ether (220 mL) and the solvent was decanted off the sticky precipitate. The off-white solid was triturated with further portions of diethyl ether until it was no longer sticky. Residual solvent was evaporated in vacuo. Yield 0.95 g.

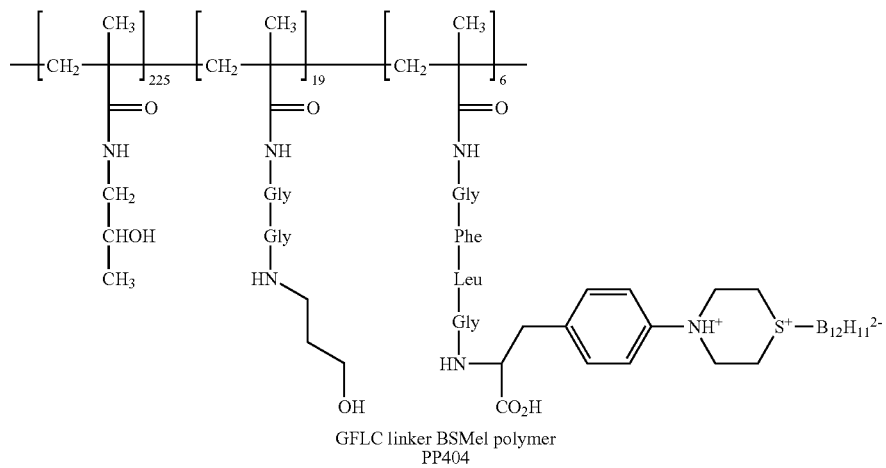

GFLC linker BSMel polymer
PP404

Example 5

Preparation of poly(HPMA-co-MA-Gly-Phe-Leu-Gly-BSMel)-Gly-Phe-Leu-Gly-Paclitaxel (PP405)
[SEQ ID NO: 20]

Powdered poly(HPMA-co-MA-GFLG-ONp) (2.15 g, 45.6 µmol) was placed in a dried flask which was sealed with a septum and flushed out with argon. Anhydrous DMSO (22 mL) was added and the mixture was stirred until all the material had dissolved BSMel (0.146 g, 366 µmol) was added. When all the solid had dissolved, triethylamine (52 µL, 366 µmol) was added causing the solution to become yellow. The solution was stirred at 20-22° C. (oil bath temperature) under argon for 5 h. Paclitaxel (0.313 g, 366 µmol) and 4-dimethylaminopyridine catalyst (0.015 g, 123 µmol) were added. After string overnight at 20-22° C., 3-amino-1-propanol (35 µL, 456 µmol) was added and the solution was stirred for a further 4 h. The solution was slowly poured into stirred diethyl ether (500 ml) and the solvent was decanted off the sticky precipitate. The yellowish solid was triturated with further portions of diethyl ether until it was no longer sticky. Residual solvent was evaporated in vacuo. Yield 2.44 g (98%).

poured into stirred diethyl ether (500 mL) and the solvent was decanted off the sticky precipitate. The red solid was triturated with further portions of diethyl ether until it was no longer sticky. Residual solvent was evaporated in vacuo. Yield 2.55 g (105%).

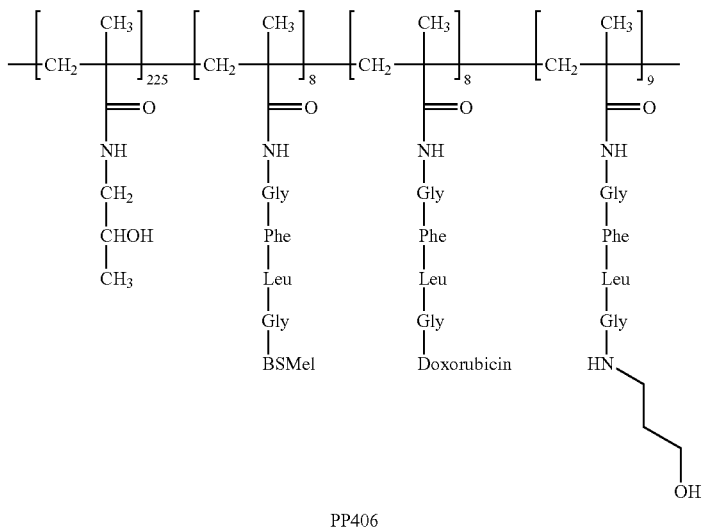

PP406

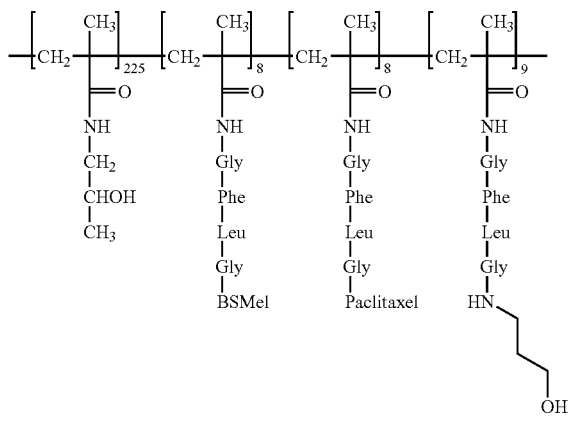

PP405

Example 6

Preparation of poly(HPMA-co-MA-Gly-Phe-Leu-Gly-BSMel) Gly-Phe-Leu-Gly-Doxorubicin (PP406) [SEQ ID NO: 20]

Powdered poly(HPMA-co-MA-GFLG-ONp) (2.15 g, 45.6 µmol) was placed in a dried flask which was sealed with a septum and flushed out with argon. Anhydrous DMSO (22 mL) was added and the mixture was stirred until all the material had dissolved. BSMel (0.146 g, 366 µmol) was added. When all the solid had dissolved, triethylamine (52 µL, 366 mol) was added. The solution was stirred at 20-22° C. (oil bath temperature) under argon for 5h. Doxorubicin hydrochloride (0.212 g, 366 µmol) and triethylamine (52 µL, 366 µmol) were added. After stirring overnight at 20-22° C., 3-amino-1-propanol (35 µL, 456 µmol) was added and the solution was stirred for a further 4 h. The solution was slowly Biodistribution Studies Female BALB/c mice (20-25 g) bearing the EMT-6 carcinoma were used. The mice-were housed four to a cage in temperature-controlled rooms and had free access to food and water. The mice were maintained in a controlled light/dark cycle, with lights on between 0700 and 1900 h In all studies, anaesthesia was maintained with ketamine (120 mg/kg) and xylazine (20 mg/kk). Animals were monitored on a daily basis for general health. Animals were euthanised, as required, under anaesthesia.

The two boronated polymers synthesized in Examples 3 and 4, namely PP403 and PP404, were injected into EMT-6 tumour-bearing mice via the tail vein. The compounds were injected in a saline solution containing 50 mg/ml (0.5 mg boron/ml). The administered volume was 0.01 mL/gbw by single bolus injection delivering a dose of approximately 5 mg boron/kg.

Concentrations of boron in tissue samples were determined using direct current plasma atomic emission spectroscopy (DCP-AES), see Coderre, J. A., Button, T. M., Micca, P. L. Fisher, C., Nawrocky, M. M., and Liu, H. B. Int. J. Radiat Oncol. Biol. Phys. (1994) 30, 643-652.

Visual observation of animal appearance, levels of activity and general behaviour indicated no evidence of toxicity (see Miura, M., Micca, P. L., Fisher, C. D., Gordon, C. R., Heinrichs, J. C. et al. Brit. J. Radiol. (1998) 847, 773-781). Tumour, blood, brain, and liver were sampled at 6, 24, 48, and 72 hours after injection for boron analyses. Four mice were used per time sampling point (16 mice in total). The boron biodistribution data are detailed in Table 2 below.

The tumour boron concentration from PP403 was about three times greater than that from PP404 which is likely to be due to the non-degradable linker in PP403. The liver tumor boron ratios were between 2:1 and 3:1 at all time points for PP403 and were between 4.5:1 and 6:1 for PP404. The tumor: blood boron ratios using PP403 were less than.1:1 until the 72 h time point, and were less than 1:1 until the 48 h time point for PP404. The absolute tumour boron concentrations are low, but the administered boron dose was also low. In comparison to biodistribution data using a similar boron dose from CuTCPH in CRM, the tumour uptake is about 2.3 times lower, but the liver uptake is 5 times lower.

TABLE 2

| Time after injection (h) | Blood (µg/g) | Tumour (µg/g) | Liver (µg/g) | Brain (µg/g) |
|---|---|---|---|---|
| | | PP403 | | |
| 6 | 13.8 ± 0.5 | 3.5 ± 0.2 | 10.4 ± 0.5 | 0.3 ± 0.1 |
| 24 | 5.7 ± 0.1 | 3.1 ± 0.3 | 7.4 ± 0.4 | 0.2 ± 0.1 |
| 48 | 4.2 ± 0.5 | 2.9 ± 0.1 | 7.7 ± 0.4 | 0.1 ± 0 |
| 72 | 2.1 ± 0.2 | 2.3 ± 0.2 | 6.9 ± 0.2 | 0.1 ± 0.1 |

TABLE 2-continued

| Time after injection (h) | Blood (µg/g) | Tumour (µg/g) | Liver (µg/g) | Brain (µg/g) |
|---|---|---|---|---|
| | | PP404 | | |
| 6 | 3.0 ± 0.3 | 1.3 ± 0 | 7.6 ± 0.3 | 0.1 ± 0 |
| 24 | 1.2 ± 0.1 | 1.1 ± 0.1 | 5.0 ± 0.5 | 0.2 ± 0 |
| 48 | 0.7 ± 0.0 | 0.8 ± 0.1 | 4.9 ± 0.2 | 0.1 ± 0 |
| 72 | 0.5 ± 0 | 0.9 ± 0.1 | 5.4 ± 0.4 | 0.1 ± 0.1 |

Table 2 shows the conjugate is able to target tumours and release the NAT agent where there is a biodegradable linker.

The invention claimed is:

1. A conjugate having the general formula $$P\text{-}(L\text{-}NCT)_n,$$

wherein

P represents an N-hydroxypropylmethacrylamide-methacrylate copolymer having a molecular weight of 5-6,000 kDa;

NCT represents a neutron capture therapy agent;

L represents a linker moiety that links the polymer to the neutron capture therapy agent; and n represents an integer from 1-1,000;

and wherein the conjugate further comprises a chemotherapeutic agent attached to the polymer via the linker moiety L.

2. A conjugate as claimed in claim 1, wherein the polymer is a 2-hydroxypropylmethacrylamide-methacrylate copolymer.

3. A conjugate as claimed in claim 1, wherein the polymer has a molecular weight of 5-100.

4. A conjugate as claimed in claim 1, wherein the ratio of hydroxypropylmethacrylamide to methacrylate is from 20:1 to 1:1.

5. A conjugate as claimed in claim 1, wherein the neutron capture therapy agent contains at least one nuclide selected from $^{6}$Li, $^{10}$B, $^{22}$Na, $^{58}$Co, $^{113}$Cd, $^{126}$I, $^{135}$Xe, $^{148m}$Pm, $^{149}$Sm, $^{151}$Eu, $^{155}$Gd, $^{157}$Gd, $^{164}$Dy, $^{184}$Os, $^{199}$Hg, $^{230}$Pa, $^{235}$U and $^{241}$Pu in sufficient quantity to undergo a neutron capture reaction.

6. A conjugate as claimed in claim 5, wherein the nuclide is $^{10}$B.

7. A conjugate as claimed in claim 1, wherein NCT represents a boronated amino acid or peptide, a modified carborane cage, a mercaptoborate, a boron-containing porphyrin or phthalocyanine, a boron-containing nucleic aid precursor, or a boron-containing foliate growth factor, hormone, radiation sensitizer, phosphates, phosphonate, phosphoramidates, cyclic thiourea derivative, amine, promazine, hydantoin or barbiturate.

8. A conjugate as claimed in claim 1, wherein the NCT makes up 1-30%, of the overall mass of the conjugate.

9. A conjugate as claimed in claim 1, wherein the linker represents a linear or branched $C_{1-15}$ alkyl which may be saturated or unsaturated, optionally substituted by carbonyl, amide, hydroxyl or halogen; a peptide in which the amino aids may be further substituted with amino, thio, carboxyl, carboxamide or imidazole groups; or a covalent bond.

10. A conjugate as claimed in claim 1, wherein n represents an integer from 1-500.

11. Poly(HPMA-co-MA-Gly-Phe-Leu-Gly-BSMe1)Gly-Phe-Leu-Gly-Paclitaxel [SEQ ID NO: 20].

12. Poly(HPMA-co-MA-Gly-Phe-Leu-Gly-BSMe1)Gly-Phe-Leu-Gly-Doxombicin [SEQ ID NO: 20].

13. A pharmaceutical composition containing the conjugate as claimed in claim 1.

14. A method of treating cancer which comprises administering to a patient in need thereof an effective amount of a medicament comprising the conjugate of claim 1.

* * * * *

UNITED STATES PATENT AND TRADEMARK OFFICE
CERTIFICATE OF CORRECTION

PATENT NO. : 7,662,360 B2
APPLICATION NO. : 10/521814
DATED : February 16, 2010
INVENTOR(S) : Bipin C. M. Patel It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 767 days.

Signed and Sealed this

Thirtieth Day of November, 2010

David J. Kappos
*Director of the United States Patent and Trademark Office*

```
                        SEQUENCE LISTING

<160> NUMBER OF SEQ ID NOS: 20

<210> SEQ ID NO 1
<211> LENGTH: 2
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 1

Gly Gly
1

<210> SEQ ID NO 2
<211> LENGTH: 3
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 2

Gly Phe Gly
1

<210> SEQ ID NO 3
<211> LENGTH: 3
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 3

Gly Phe Phe
1

<210> SEQ ID NO 4
<211> LENGTH: 3
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 4

Gly Leu Gly
1
```

```
<210> SEQ ID NO 5
<211> LENGTH: 3
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 5

Gly Val Ala
1

<210> SEQ ID NO 6
<211> LENGTH: 3
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 6

Gly Phe Ala
1

<210> SEQ ID NO 7
<211> LENGTH: 3
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 7

Gly Leu Phe
1

<210> SEQ ID NO 8
<211> LENGTH: 3
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 8

Gly Leu Ala
1

<210> SEQ ID NO 9
<211> LENGTH: 3
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 9

Ala Val Ala
1

<210> SEQ ID NO 10
<211> LENGTH: 4
<212> TYPE: PRT
<213> ORGANISM: Artificial Sequence
<220> FEATURE:
<223> OTHER INFORMATION: polypeptide linker group used in a molecule
      with a high affinity for human tumors
```

```
<220> FEATURE:
<221> NAME/KEY: MISC_FEATURE
<222> LOCATION: (1)..(1)
<223> OTHER INFORMATION: residue may be modified with HPMA-co-MA
<220> FEATURE:
<221> NAME/KEY: MISC_FEATURE
<222> LOCATION: (2)..(2)
<223> OTHER INFORMATION: residue may be replaced by BPA
<220> FEATURE:
<221> NAME/KEY: MISC_FEATURE
<222> LOCATION: (4)..(4)
<223> OTHER INFORMATION: residue may be modified with BSH, BPA, CuTCPH,
      CuTCPHBr, carborane butamine (B10C2H11(CH2)3CHCO2NH2)

<400> SEQUENCE: 10

Gly Phe Leu Gly
1

<210> SEQ ID NO 11
<211> LENGTH: 4
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 11

Gly Phe Phe Leu
1

<210> SEQ ID NO 12
<211> LENGTH: 4
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 12

Gly Leu Leu Gly
1

<210> SEQ ID NO 13
<211> LENGTH: 4
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 13

Gly Phe Tyr Ala
1

<210> SEQ ID NO 14
<211> LENGTH: 4
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 14

Gly Phe Gly Phe
1

<210> SEQ ID NO 15
<211> LENGTH: 4
<212> TYPE: PRT
```

```
<213> ORGANISM: Artificial Sequence
<220> FEATURE:
<223> OTHER INFORMATION: polypeptide linker group used in a molecule
      with a high affinity for human tumors

<400> SEQUENCE: 15

Ala Gly Val Phe
1

<210> SEQ ID NO 16
<211> LENGTH: 4
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 16

Gly Phe Phe Gly
1

<210> SEQ ID NO 17
<211> LENGTH: 5
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 17

Gly Phe Leu Gly Phe
1               5

<210> SEQ ID NO 18
<211> LENGTH: 6
<212> TYPE: PRT
<213> ORGANISM: Artificial Sequence
<220> FEATURE:
<223> OTHER INFORMATION: polypeptide linker group used in a molecule
      with a high affinity for human tumors

<400> SEQUENCE: 18

Gly Gly Phe Leu Gly Phe
1               5

<210> SEQ ID NO 19
<211> LENGTH: 4
<212> TYPE: PRT
<213> ORGANISM: Artificial Sequence
<220> FEATURE:
<223> OTHER INFORMATION: polypeptide linker group used in a molecule
      with a high affinity for human tumors
<220> FEATURE:
<221> NAME/KEY: MISC_FEATURE
<222> LOCATION: (1)..(1)
<223> OTHER INFORMATION: modified with HPMA-co-MA
<220> FEATURE:
<221> NAME/KEY: MISC_FEATURE
<222> LOCATION: (2)..(2)
<223> OTHER INFORMATION: modified with BPA
<220> FEATURE:
<221> NAME/KEY: MISC_FEATURE
<222> LOCATION: (4)..(4)
<223> OTHER INFORMATION: modified with BPA

<400> SEQUENCE: 19

Gly Leu Gly Gly
1
```

-continued

```
<210> SEQ ID NO 20
<211> LENGTH: 8
<212> TYPE: PRT
<213> ORGANISM: Artificial Sequence
<220> FEATURE:
<223> OTHER INFORMATION: polypeptide linker group used in a molecule
      with a high affinity for human tumors
<220> FEATURE:
<221> NAME/KEY: MISC_FEATURE
<222> LOCATION: (1)..(1)
<223> OTHER INFORMATION: modified with HPMA-co-MA
<220> FEATURE:
<221> NAME/KEY: MISC_FEATURE
<222> LOCATION: (4)..(4)
<223> OTHER INFORMATION: modified with BSH or BSMel
<220> FEATURE:
<221> NAME/KEY: MISC_FEATURE
<222> LOCATION: (8)..(8)
<223> OTHER INFORMATION: modified with an anticancer agent selected
      from doxorubicin, ellipticin, cisplatin and paclitaxel

<400> SEQUENCE: 20

Gly Phe Leu Gly Gly Phe Leu Gly
1               5
```